United States Patent [19]

Carner, Jr.

[11] Patent Number: 4,704,014

[45] Date of Patent: Nov. 3, 1987

[54] ARTICLE OF HEADWEAR PROVIDING SUPPLEMENTAL WIDE ANGLE PERIPHERAL VISION

[76] Inventor: Donald C. Carner, Jr., 5440 "T" Street, Sacramanto, Calif. 95819

[21] Appl. No.: 742,563

[22] Filed: Jun. 7, 1985

[51] Int. Cl.⁴ .............................................. G02C 1/00
[52] U.S. Cl. ........................................ 351/43; 351/50
[58] Field of Search .................... 351/41, 43, 50, 158; 350/145, 146, 617, 618, 638; 2/430

[56] References Cited

U.S. PATENT DOCUMENTS

| | | | |
|---|---|---|---|
| 2,594,698 | 4/1952 | Thomas | 351/50 |
| 2,909,959 | 10/1959 | Girden | 351/43 |
| 3,059,519 | 10/1962 | Stanton | |
| 3,672,750 | 6/1972 | Hagen | |
| 3,787,109 | 1/1974 | Vizenor | |
| 4,156,292 | 5/1979 | Helm et al. | |
| 4,231,117 | 11/1980 | Aileo | |

Primary Examiner—Rodney B. Bovernick
Assistant Examiner—P. M. Dzierzynski
Attorney, Agent, or Firm—Leonard Bloom

[57] ABSTRACT

A field of vision enhancement device having a mounting on an article of headwear adjustable with respect to a straight ahead, normal line of sight including optics for displaying at least one field of optical information either normally occluded by the headwear article or not readily discernable with binocular vision whereby the field of vision is enhanced.

17 Claims, 8 Drawing Figures

ARTICLE OF HEADWEAR PROVIDING SUPPLEMENTAL WIDE ANGLE PERIPHERAL VISION

BACKGROUND OF THE INVENTION

This invention relates generally to improvements in optical devices, and more particularly is directed to a wide angle viewing device to be incorporated into headgear including but not limited to protective masks and helmets. It is particularly suited for use in conjunction with conventional helmet and face mask gear used in space and underwater environments. However it may also be used in any situation where a substantial increase in peripheral vision is desirable.

Humans operating in space and underwater are at a distinct sensory disadvantage because environmental conditions and conventional protective head gear tends to restrict the visual field of view and at the same time renders the senses of hearing, smell and touch useless. This restriction of sensory inputs occurs in underwater and space environments where the region from which an individual is likely to receive physical influence is often greatly expanded. In contrast to normal terrestrial activities, the expanded region of probable physical influence or "sphere of influence" is generally greater in underwater and space environments. Often in space and underwater one may receive physical influence from any direction radiating from an imaginary sphere surrounding the individual. It is therefore important to provide an individual working in these environments with a means of monitoring all or most of this expanded sphere of influence.

In underwater environments most free swimming creatures have evolved non binocular, independent, extreme wide angle, peripheral or "fisheye" vision. The instant invention derives from these examples in nature to provide an individual with independent supplemental vision of left and right hemispheres of influence. The intent is not to expand or modify the function of normal binocular vision but to supplement it with an extreme wide angle peripheral viewing system which can be positioned so as to minimally restrict normal human vision. The instant design in its various embodiments can easily be attached to the exterior of a mask or helmet viewing surface or integrated within the structure, being placed between the eye and the viewing surface and offset somewhat from one's direct line of sight when the eye is centered.

SUMMARY AND OBJECTS OF THE INVENTION

The instant invention is a supplemental extreme wide-angle viewing system for mounting on or within protective headgear providing supplemental peripheral vision. A principal objective of the invention is to provide its user with an extreme wide angle, or "fisheye" view of a hemisphere from which physical influence on the user's body can be expected. Two of these viewing devices may be used to provide visual coverage of substantially the entire sphere of influence surrounding the user.

Another objective is to provide a supplementary extreme wide-angle view with a minimally distracting influence on normal binocular vision.

Another objective is to produce this extreme wide-angle supplementary view in a compact package which can easily be retrofitted to existing protective head gear or integrated into new designs.

Another objective is to provide a supplemental wide angle perpherial viewing system for cameras and other non animal imaging systems.

A further object contemplates providing the device as characterized above which lends itself to mass production techniques, is safe to use and is durable in construction.

A further objective is to provide a viewing device having a mounting on an article of headwear which can be adjusted with respect to a normal line of sight including an optical arrangement for displaying at least one field of optical information either normally occluded by the headwear article or not readily discernable with binocular vision whereby the field of vision is enhanced.

A further object provides a device as in the preceeding paragraph wherein the optical arrangement includes a supporting member having at least one diverging lens and at a distal end therefrom a mirror or penta prism for changing the line of sight at an angle "a" thereby aligning with said diverging lens and the eye of the user so that the eye, the diverging lens, and the mirror or prism for changing the line of sight are optically coupled. Angle "a" is prefered to be 90 degrees or greater since the mirror or prism at an angle less than 90 degrees would obstruct the user's normal forward field of vision.

A further object includes a converging lens element interposed between the eye and the diverging lens as set forth in the paragraph immediately above. Alternatively a pair of diverging lenses can be provided with the concave face of each lens facing the other.

Another objective includes the mounting of the device specified in the two immediately preceeding paragraphs on an article of headwear by a clamp which is used for adjusting the device's body portion which circumscribes the optics therein either by translation along a longitudnal axis or rotation within the clamp.

Alternatively the mounting may include a seal adapted to pass through the sidewall of the article of headwear. The protective body portion may be formed from a solid transparent optical grade resin or an annular housing having an outwardly flared end and within which the diverging lens elements are adapted to be placed, and a separator tube is provided to hold the lens element in spatial relationship from the converging lens element whereby optical coupling is achieved.

Other and further objectives of this invention will be apparent from the following description.

BRIEF DESCRIPTION OF THE DRAWINGS

In the accompanying drawings to which reference is made in the instant specification and in which like reference characters are used to indicate like parts in the various views.

| NUMBER | PARTS LIST |
|---|---|
| 10 | MASK/HELMET BODY |
| 11 | MASK/HELMET FACEPLATE |
| 12 | MASK ADJUSTMENT STRAP |
| 13 | CLAMP FOR EXTERNAL APPLICATION |
| 14 | SEAL FOR INTERNAL APPLICATION |
| 15 | WIDE ANGLE VIEWING DEVICE |
| 16 | DIVERGING LENS ELEMENT (S) |
| 17 | CONVERGING LENS ELEMENT |
| 18 | DIAGONAL MIRROR OR REFLECTING PRISM |
| 19 | REFLECTING PENTA PRISM |
| 20 | VIEWING EYE |
| 21 | OPTICAL AXIS |
| 22 | PROTECTIVE BODY |
| 23 | AIR, WATER, OR VACUUM SPACE |
| 24 | LENS SEPARATOR TUBE |
| 25 | SOLID OPTICAL GRADE RESIN |
| 26 | NORMAL VISION AXIS |
| 27 | DEVICE VIEWING AXIS |
| 28 | ANGLE "a" |

DETAILED DESCRIPTION OF THE PREFERRED EMBODIMENT

Figures 1, 2:
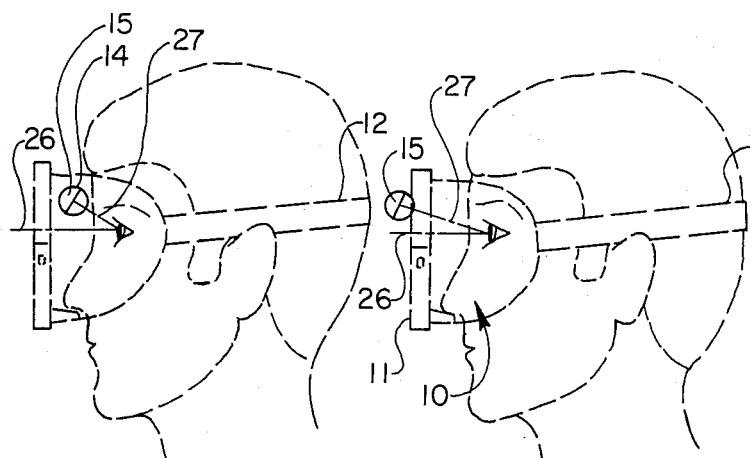
FIG. 1 is a side view showing placement of the invention penetrating the protective mask.
FIG. 2 is a side view showing placement of the invention outside of the protective mask.
Figure 3:
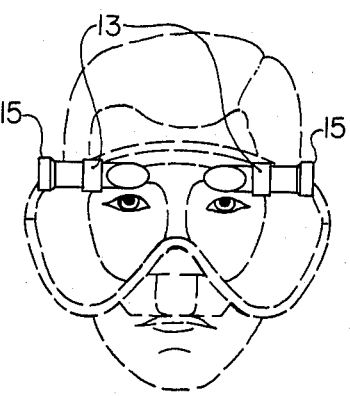
FIG. 3 is a front view showing placement of the invention relative to the users normal line of sight.

Referring now to FIGS. 1-3, a wide angle viewing apparatus, indicated generally by numeral 15, is attached to a conventional protective underwater mask 10, which includes a transparent faceplate 11 and a positioning strap 12.

Distinction should be made between a "wide-angle" viewing apparatus and one which affords a "hemispherical" view. Both are attainable through the instant invention when the appropriate lens elements are utilized. The primary diference between the two involves the degree to which a given total field of vision is to be viewed. The wide-angle field is somewhat less than the hemispherical field. These terms in the ensuing text however will be used interchangeably.

The viewing device includes a clamp 13, formed from plastic or metal and serving as a fixture which attaches to the mask faceplate 11 by an appropriate adhesive such as silicone or a cyanoacrylate based product. The clamp 13 or alternatively a mask penetrating seal 14 (FIG. 1) is used to support and position the wide-angle viewing apparatus 15 as. Both the clamps 13 and seals 14 are configured to allow positioning of the wide angle viewing apparatus for accomodating the spacing of the eyes of the individual user.

As shown diagrammatically in FIG. 1 and FIG. 2, the normal viewing axis 26 can be defined as the line of sight extending normally from the eye when the eye is centered in the head. These devices are best placed above or below and to the outside of the normal viewing axis so when the user desires a view of the left hemispherical environment, the user's eye is brought up (or down) and to the left of the normal axis 26, to the device viewing axis 27. Similarly, to view the right hemisphere the eye is brought up and to the right of the the normal axis 26. Placement of the supplementary wide angle viewing device 15, away from the normal field of vision is important because it makes use of normal binocular vision functions when focusing on either the right or the left hemispherical view. Thus, by requiring the user to look off axis to either the right or the left to view the device, the user's normal visual response allows the image from the eye in the direction of the off axis view to dominate. That is, by requiring the eye associated with the hemisphere to be viewed to be moved from its line of sight axis (26) this eye will dominate the other eye in interpreting information, providing a clear view of that hemisphere. This facilitates easy interpretation of the individual left or right hemispheres when that viewing device is accessed. Moreover, when both eyes are in the normal forward looking position as suggested by line of sight 26, the images produced by the devices 15 are not substantially intrusive to the field of view.

Figure 4:
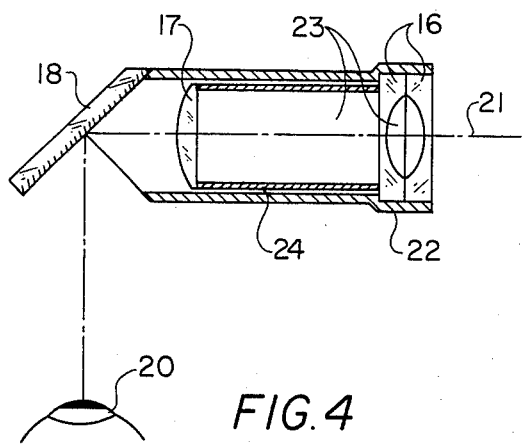
FIG. 4 is a section view of the invention where any combination of air, water, or vacuum separates the various lens elements.

FIG. 4 reflects one possible optical arrangement for effecting the hemispherical viewing according to the present invention. The optical elements which provide this effect as shown in FIG. 4, include at least one diverging lens element 16 but preferably a pair of diverging elements being the furthest lenses from the eye 20. Proceeding successively closer to the eye, a converging lens 17 is provided and a diagonal mirror or prism 18 changes the line of sight towards the eye. Typical specifications for the lens elements might be for numeral 16 a pair of spherical plano-concave lenses each with a power of minus 50.0 diopters and a spherical plano-convex lens with a power of plus 21.5 diopters.

The lenses of FIG. 4 are held in a fixed, spaced relationship by an appropriate mounting to be discussed and can be supported in air or other transparent medium as referenced by numeral 23. The lens elements are held in proper position by lens seperator tube 24. Thus the converging lens 17 is spaced from the pair of diverging lenses 16 by means of an annular tube 24. In turn, the diverging lens 16 is carried in a protective body having generally annular configuration and a stepped out portion at the end of the tube adjacent the diverging lenses 16. The protective body 22 is frictionally disposed within either the clamp 13 or the seal 14 so that longitudinal translation of the wide-angle viewing device can be effected. The fit between the seal (FIG. 1) is of sufficiently close tolerance to preclude the admission of water into the mask 10 and may be enhanced by the use of "O" rings (not shown). The end of the protective body 22 remote from the diverging lens 16 supports the diagonal mirror 18 or reflective prism 19.

It is contemplated that other interstitial media having different indicies of refraction may be incorporated in the design and thus the air space 23 could be replaced with water, glass, vacuum optical grade transparent resin, or any other suitable transparent medium.

The lenses in FIGS. 4-8, while of conventional design, could be substituted with other lens types, particularly Fresnel lenses which are also commercially available. Moreover, the lens elements may be made from any suitable optically refractive material including but not limited to glass and plastic. This invention also contemplates substitution of lens elements of different types, focal lengths, and diameters. Thus the foregoing optical specifications are seen to be illustrative and not limited except as set forth in the claims. Similarly the body 22 as well as the lens separator tube 24 could be formed from an inexpensive plastic material such as PVC or polypropylene. Likewise the diagonal mirror 18 could be made from a plastic material such as a mirrorized acrylic sheet.

Figure 5:
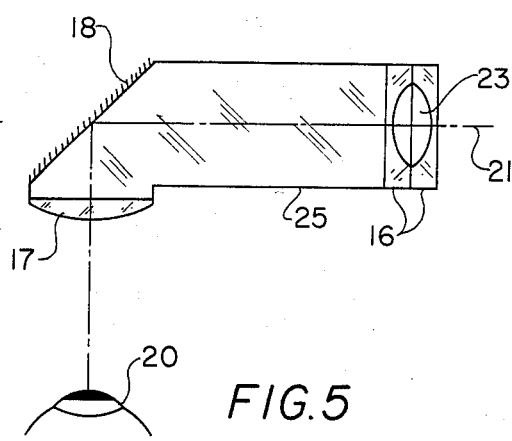
FIG. 5 is a section view of the invention where diverging and converging optical elements are separated by a transparent optical grade resin.

FIG. 5 depicts an alternative embodiment of the invention in which the body 22, and separator 24, have been replaced by a solid optically transparent lens separator 25. In this embodiment, the diagonal mirror is interposed between the converging lens element 17 and the diverging lens 16. Note that the airspace 23 separating the diverging lens elements 16 has been preserved.

Figure 6:
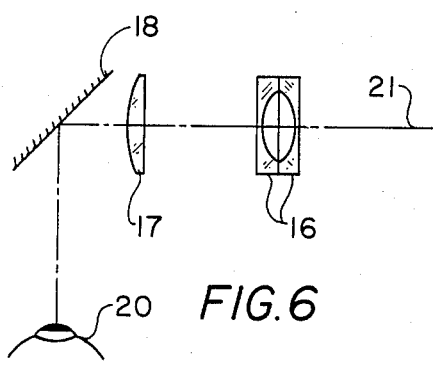
FIG. 6 is an optical path diagram of the invention where both diverging and converging lens elements are placed in front of the diagonal mirror.
Figure 7:
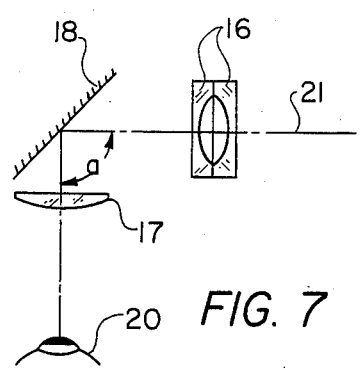
FIG. 7 is an optical path diagram of the invention where the diagonal mirror is placed between diverging and converging lens elements.

FIGS. 6 and 7 respectively parallel the devices of FIGS. 4 and 5 absent the support media and reflect the optical axis 21 that results when utilzing the device according to the present invention. Both of these configurations produce an image erect, left-right reversed image at the viewing position.

Figure 8:
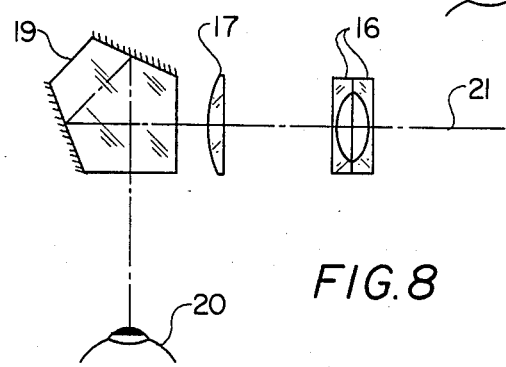
FIG. 8 is an optical path diagrams of the invention where the diagonal mirror is replaced with a reflecting penta prism.

With respect to FIG. 8, accomodation has been made to avoid the left-right reversed image which is shown in FIGS. 4 through 7. Here, a conventional reflecting penta prism 19 produces the necessary image transformation to produce and erect image which is a correct left-right reading. Clearly, the placement of the converging lens element 17 can be made such that it is interposed between the eye 20 and the penta prism 19.

In use and operation the protective body 22 is placed either within the seal 14 with suitable gasketing to preclude water intrusion with respect to the seal or in an external clamp 13. The protective body 22 is translated axially to orient the apparatus appropriately above and outside of the conventional line of sight. Left and right hemispheres of vision can then be experienced by the person wearing the apparatus, and by virtue of placing the devices away from the normal line of sight 26, forward vision can occur only minimally impeded and when viewing through either of the two devices the eye closest to the device being used will dominate.

Having thus described the inventioned it should be apparent that numerous structural modifications are contemplated as being part of this invention as set forth herein above and as defined here and below in the claims. For example while a mask 10 has be illustrated, it should be evident that this device is equally adaptable to utilization with full or partial helmets, hard hats, headbands, or any other article of headwear.

I claim:

1. In an article of headwear providing supplemental wide angle peripheral vision, wherein the user's eye has a normal viewing axis, the combination of a device and means for clamping the device on the article of headwear, the device including a body disposed in front of the user's face and arranged substantially horizontally between the nose bridge and temple of the user, means for adjusting the device relative to the user, the body including respective end portions including a first end portion disposed substantially adjacent to the user's nose bridge but offset vertically with respect to the normal viewing axis of the user's eye, a reflective means carried by the first end portion of the body, so that the user's eye may shift vertically up or down away from the normal viewing axis to look at the reflective means, the reflective means being disposed in a plane which is angled with respect to the line of sight of the user's eye in looking at the reflective means, thereby establishing an optical path alternatively of the normal viewing axis, the body further having a second end portion remote from the first end portion thereof, a divergent lens means carried by the second end portion of the body, optical transmission means in the optical path between the divergent lens means and the reflective means, and a converging lens means carried by the body and arranged between the user's eye and the divergent lens means.

2. The combination of claim 1, wherein said divergent lens means comprises first and second diverging lenses, each of which has an arcuate surface and a planar surface.

3. The combination of claim 2, wherein said first and second diverging lenses are oriented such that said arcuate surfaces face each other.

4. The combination of claim 3, wherein said first and second diverging lenses are proximately disposed to each other, and said arcuate surfaces are concave with respect to each other so that a transparent space is enclosed therebetween.

5. The combination of claim 4, wherein said converging lens means comprises a converging lens interposed between the viewer and said reflective means along said optical path.

6. The combination of claim 1, including a second said device oriented to similarly address the other eye of the user, independent of said first device, and further including means for
adjustably supporting each said device laterally of the user, whereby each eye of the user accommodates diverse interpupillary spacing of different users.

7. The combination of claim 6, wherein said optical path between said first and second end portions of the body are circumscribed by an outer boundary defining a housing, and wherein
said adjustable supporting means circumscribes a portion of said housing such that translation of said housing along the length thereof accommodates different users.

8. The combination of claim 7, wherein said first end portion of the body of said device supports a reflective surface to direct optical information from said divergent lens means to the user's eye.

9. The combination of claim 8, wherein said adjustable supporting means comprises a clamp fixed to said article of headwear, and wherein said housing passes through said clamp.

10. The combination of claim 8, wherein said ajustable supporting means comprises a wall having an opening formed therein for frictionally receiving and supporting said device.

11. The combination of claim 1, wherein said optical path is defined by a solid block of optically transparent material disposed within the body of the device.

12. The combination of claim 1, wherein said body includes a tubular outer housing having a belled end adjacent to and overlying said diverging lens means, and a second inner housing, concentrically disposed within said outer housing and supported by said diverging lens means at a planar surface thereof, said second housing supporting said converging lens means.

13. The combination of claim 11, wherein said solid block of optically transparent material supports said reflective means, and wherein said reflective means comprises a mirror.

14. The combination of claim 1, wherein said reflective means comprises a pentaprism.

15. The combination of claim 1, wherein the converging lens means is disposed between the reflective means and the divergent lens means.

16. The combination of claim 1, wherein the converging lens means is disposed between the reflective means and the eye of the user.

17. The combination of claim 1, wherein the converging lens means includes a convex surface facing the reflective means.

* * * * *